US010386359B2

(12) United States Patent
Paris et al.

(10) Patent No.: US 10,386,359 B2
(45) Date of Patent: Aug. 20, 2019

(54) METHODS FOR DETERMINING WHETHER A PATIENT WILL ACHIEVE A RESPONSE AFTER RADIATION THERAPY

(71) Applicants: INSERM (INSTITUT NATIONAL DE LA SANTE ET DE LA RECHERCHE MEDICALE), Paris (FR); UNIVERSITE DE NANTES, Nantes (FR); UNIVERSITE D'ANGERS, Angers (FR); CENTRE NATIONAL DE LA RECHERCHE SCIENTIFIQUE (CNRS), Paris (FR); INSTITUT DE CANCEROLOGIE DE L'OUEST—SITE RENE GAUDUCHEAU, Saint-Herblain (FR)

(72) Inventors: Francois Paris, Nantes (FR); Nolwenn Dubois, Nantes (FR); Emmanuel Rio, Nantes (FR); Natacha Ripoche, Nantes (FR)

(73) Assignees: INSERM (INSTITUT NATIONAL DE LA SANTE ET DE LA RECHERCHE MEDICALE), Paris (FR); UNIVERSITE DE NANTES, Nantes (FR); UNIVERSITE D'ANGERS, Angers (FR); CENTRE NATIONAL DE LA RECHERCHE SCIENTLFIQUE (CNRS), Paris (FR); INSTITUT DE CANCERLOGIE DE L'OUEST—SITE RENE GAUDUCHEAU, Saint-Herblain (FR)

( * ) Notice: Subject to any disclaimer, the term of this patent is extended or adjusted under 35 U.S.C. 154(b) by 0 days.

(21) Appl. No.: 15/313,338

(22) PCT Filed: May 22, 2015

(86) PCT No.: PCT/EP2015/061354
§ 371 (c)(1),
(2) Date: Nov. 22, 2016

(87) PCT Pub. No.: WO2015/177329
PCT Pub. Date: Nov. 26, 2015

(65) Prior Publication Data
US 2017/0184566 A1 Jun. 29, 2017

(30) Foreign Application Priority Data

May 23, 2014 (EP) ..................................... 14305764
Mar. 24, 2015 (EP) ..................................... 15305426

(51) Int. Cl.
*G01N 33/50* (2006.01)
*C12Q 1/48* (2006.01)
*G01N 33/92* (2006.01)

(52) U.S. Cl.
CPC ........... *G01N 33/5011* (2013.01); *C12Q 1/48* (2013.01); *G01N 33/502* (2013.01); *G01N 33/5008* (2013.01); *G01N 33/92* (2013.01); *G01N 2560/00* (2013.01)

(58) Field of Classification Search
CPC . G01N 33/5011; G01N 33/92; G01N 2560/00
See application file for complete search history.

(56) References Cited

U.S. PATENT DOCUMENTS

| 6,274,309 | B1 | 8/2001 | Kolesnick et al. | |
| 2012/0027873 | A1* | 2/2012 | Schlingensiepen | ......................... A61K 31/7088 424/649 |
| 2013/0315836 | A1* | 11/2013 | Gao | ................... A61K 49/0041 424/9.6 |
| 2015/0139915 | A1* | 5/2015 | Worgall | ............... A61K 31/353 424/43 |

FOREIGN PATENT DOCUMENTS

| WO | 99/28747 A2 | 6/1999 |
| WO | 01/55410 A2 | 8/2001 |
| WO | 2011/059776 A2 | 5/2011 |

OTHER PUBLICATIONS

Lauber, Kirsten et al. "Dying cell clearance and its impact on the outcome of tumor radiotherapy." Frontiers in Oncology (2012) 2 116. (Year: 2012).*
Linder, Stig et al. "Determining tumor apoptosis and necrosis in patient serum using cytokeratin 18 as a biomnarker." Cancer Letters (2004) 214 1-9. (Year: 2004).*
International Search Report of PCT/EP2015/061354, dated Jul. 15, 2015.
Ogretmen B. et al., "Biologically active sphingolipids in cancer pathogenesis and treatment", Nature Reviews Cancer, vol. 4, No. 8, Aug. 2004, pp. 604-616. Charleston, South Carolina.
Ogretmen B. et al., "Updates on functions of ceramide in chemotherapy-induced cell death and in multidrug resistance", Drug Resistance Updates, vol. 4, No. 6, Dec. 2001, pp. 368-377. Charleston, South Carolina.
Karshafian R. et al., "Enhancement of radiation therapy by ultrasonically-stimulated microbubbles in vitro: Effects of treatment scheduling on cell viability and production of ceramide", 2010 IEEE Internationational Ultrasonics Symposium Proceedings, Oct. 2010, pp. 2115-2118. Toronto, Canada.

(Continued)

*Primary Examiner* — Christopher Adam Hixson
(74) *Attorney, Agent, or Firm* — Young & Thompson

(57) ABSTRACT

Disclosed are methods for determining whether a patient will achieve a response after radiation therapy, in particular a method for determining whether a patient suffering from a cancer will achieve a response after radiation therapy including the steps of i) determining the level of ceramide in a first blood sample obtained from the patient before radiation therapy, ii) determining the level of ceramide in a second blood sample obtained from the patient during or just after radiation therapy, iii) comparing the level determined at step i) with the level determined at step ii) and iv) concluding that the patient will achieve response when the level determined at step ii) is higher than the level determined at step i) or concluding that the patient will not achieve a response when the level determined at step ii) is lower than the level determined at step i).

15 Claims, 5 Drawing Sheets

(56) References Cited

OTHER PUBLICATIONS

Figure 1:
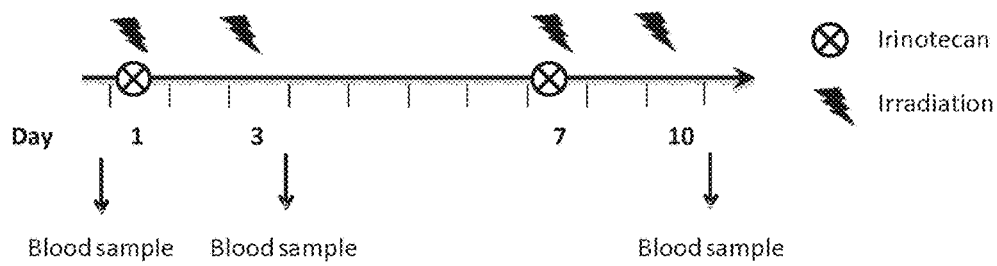

Malki A. et al., "Differential apoptotic effects of novel quinuclidinone analogs 8a and 8b in normal and lung cancer cell lines", Anticancer Research, vol. 31, Apr. 2011, pp. 1345-1358. Alexandria, Egypt.

Riboni L. et al., "Ceramide levels are inversely associated with malignant progression of human glial tumors", GLIA, vol. 39, No. 2, Jun. 2002, pp. 105-113. Segrate, Italy.

Guillermet-Guibert J. et al., "Targeting the sphingolipid metabolism to defeat pancreatic cancer cell resistance to the chemotherapeutic gemcitabine drug", Molecular Cancer Therapeutics, vol. 8, No. 4, Apr. 2009, pp. 809-820. Toulouse, France.

Ruckhaberle E. et al., "Gene expression of ceramide kinase, galactosyl ceramide synthase and ganglioside GD3 synthase is associated with prognosis in breast cancer", Journal of Cancer Research and Clinical Oncology, vol. 135, No. 8, Jan. 2009, pp. 1005-1013. Frankfurt, Germany.

Kumar S. et al., "Biomarkers in cancer screening, research and detection: present and future: a review", Biomarkers, vol. 11, No. 5, 2006, pp. 385-405. New Delhi, India.

Malviya G. et al., "PET imaging to monitor cancer therapy", Current Pharmaceutical Biotechnology, vol. 14, No. 7, 2013, pp. 669-682. Basel, Switzerland.

Ganepola G. A. et al., "Use of blood-based biomarkers for early diagnosis and surveillance of colorectal cancer", World Journal of Gastrointestinal Oncology, vol. 6, No. 4, 2014, pp. 83-97. Paramus, NJ.

Corre I. et al., "Plasma membrane signaling induced by ionizing radiation", Mutation Research, vol. 704, No. 1-3, 2010, pp. 61-67. Nantes, France.

Kimura K. et al., "Role of ceramide in mediating apoptosis of irradiated LNCaP prostate cancer cells", Cell Death and Differentiation, vol. 10, No. 2, 2003, pp. 240-248. Washington, DC.

Rodriguez-Lafrasse C. et al., "Increasing endogenous ceramide using inhibitors of sphingolipid metabolism maximizes ionizing radiation-induced mitochondrial injury and apoptotic cell killing", Int Journal Cancer, vol. 101, No. 6, 2002, pp. 589-598. Oullins Cedex, France.

Garcia-Barros M. et al., "Tumor response to radiotherapy regulated by endothelial cell apoptosis", Science, vol. 300, No. 5622, May 2003, pp. 1155-1159. Washington, DC.

Petrache I. et al., "Ceramide upregulation causes pulmonary cell apoptosis and emphysema-like disease in mice", Nat Med, vol. 11, No. 5, May 2005, pp. 491-498. Baltimore, MD.

Watt M. J. et al., "Regulation of plasma ceramide levels with fatty acid oversupply: evidence that the liver detects and secretes de novo synthesised ceramide", Diabetologia, vol. 55, No. 10, Oct. 2012, pp. 2741-2746. Clayton, Australia.

Sathishkumar S. et al., "Elevated sphingomyelinase activity and ceramide concentration in serum of patients undergoing high dose spatially fractionated radiation treatment: implications for endothelial apoptosis", Cancer Biology and Therapy, vol. 4, No. 9, 2005, pp. 979-986. DOI: 10.4161/cbt.4.9.1915, Lexington, Kentucky USA.

Bibault J. E. et al., "CT appearance of pulmonary carcinomas after stereotactic radiation therapy", Diagnostic and Interventional Imaging, vol. 94, No. 3, 2013, pp. 255-262. Lille Cedex, France.

Marathe S. et al., "Human vascular endothelial cells are a rich and regulatable source of secretory sphingomyelinase. Implications for early atherogenesis and ceramide-mediated cell signaling", Journal of Biological Chemisrty, vol. 273, No. 7, Feb. 1998, pp. 4081-4088. Philadelphia, Pennsylvania.

Tepper A. D. et al., "Ordering of ceramide formation, caspase activation, and mitochondrial changes during CD95-and DNA damage-induced apoptosis", The Journal of Clinical Investigation, vol. 103, No. 7, Apr. 1999, pp. 971-978. Amsterdam, The Netherlands.

Bernier J. et al., "Radiation oncology: a century of achievements", Nature Reviews; Cancer, vol. 4, No. 9, 2004, pp. 737-747. Bellinzona, Switzerland.

Lang P. A. et al., "Liver cell death and anemia in Wilson disease involve acid sphingomyelinase and ceramide", Nature Medicine, vol. 13, No. 2, Feb. 2007, pp. 164-170. Tubingen, Germany.

Kavanagh B. D. et al., "Advances in treatment techniques: stereotactic body radiation therapy and the spread of hypofractionation", Cancer Journal, vol. 17, No. 3, 2011, pp. 177-181. Aurora, CO.

Delogu G. et al., "Ceramide concentrations in septic patients: a possible marker of multiple organ dysfunction syndrome", Critical Care Medicine, vol. 27, No. 11, 1999, pp. 2413-2417.

Eisen M. B. et al., (1998) "Cluster analysis and display of genome-wide expression patterns", Proc Natl Acad Science USA, vol. 95, No. 25, 1998, pp. 14863-14868. Stanford, CA.

Bodennec J. et al, "A procedure for fractionation of sphingolipid classes by solid-phase extraction on aminopropyl cartridges", Journal of Lipid Research, vol. 41, No. 9, pp. 1524-1531 France.

Cox D.R., "Regression Models and Life Tables", Journal of the Royal Statistical Society. Series B (Methodological), vol. 34, No. 2. (1972), pp. 187-220. London, England.

Hara A. et al., "Lipid extraction of tissues with a low-toxicity solvent.", Analytical Biochemistry, vol. 90, No. 1, (1978) pp. 420-426. Ann Arbor, Michigan.

Kaplan E.L. et al., "Non parametric estimation from incomplete observations.", Journal of the American Statistical Association, vol. 53, No. 282 (Jun. 1958), pp. 457-481, Chicago, USA.

Chang, Howard Y. and Yang, Xiaolu, "Proteases for Cell Suicide: Functions and Regulation of Caspases," Microbiology and Molecular Biology Reviews, vol. 64, No. 4, Dec. 2000, pp. 821-849.

\* cited by examiner

METHODS FOR DETERMINING WHETHER A PATIENT WILL ACHIEVE A RESPONSE AFTER RADIATION THERAPY

FIELD OF THE INVENTION

The present invention relates to methods for determining whether a patient will achieve a response after radiation therapy.

BACKGROUND OF THE INVENTION

Radiation therapy is one of the most common therapeutic and palliative anti-cancer treatments. Its main limitation is due to the intrinsic radiation resistance of the tumor, limiting its efficacy (1). Because of the improvement of tumor imaging and medical physic researches new stereotaxic radiation therapy devices have been developed with a better targeting of the radiation into the tumor. Those stereotaxic accelerators are changing irradiation plans by increasing the dose within a limited number of fractions (1). If they demonstrated a strong efficacy in oligometastases and small solid tumors, these hypofractionated radiation therapy protocols have to be validated for most of the tumor type in function of their localisation and their radiation resistance.

Actually, the most common way to validate the radiation therapy efficacy is obtained through the visualisation of the tumor volume control or regression by CT-scan or by other non-invasive imaging techniques. Unfortunately, tumor volume response can be estimated within months after the end of the radiation therapy delaying any alternative treatment. Discovering biological markers allowing the discrimination between responding and refractory patients to the radiation therapy represents a major issue to improve anti-tumor treatment.

Biomarkers can be classified in three categories: omics from tumor biopsies, phenotypic imaging and secretory factors (2). Tumor markers by Omics are essentially obtained by genomics and proteomic assays. If they have the advantage to quest markers in a very large broad of molecular events, the need for tumor biopsies limits their studies to specific tumor localisation and the number of samples. Usually, those studies are dedicated to prognostic studies grading and assessing the treatment. Phenotypic imaging allows the evaluation of some physiologic change in the tumor such as hypoxia, cell proliferation index, necrosis or immune cell infiltration (3). Phenotypic imaging has the advantage to be non-invasive. However, the heterogeneity of the tumor response and the consistent quantification of the molecular biomarkers remain under investigation. Finally, secretory factors coming from blood, saliva and urine samples have the advantage to be easy obtained by any patient and can be provided before and all along the treatment (4). Those secretory factors can include pro-inflammatory cytokines, peptides LDL or circulating tumor cells. If some of them have been investigated, none of them have been validated as biomarker of the radiation therapy efficacy.

Sphingolipid ceramide also represent a potential and interesting secreted biomarker. Indeed, ceramide is a pro-apoptotic factor, generated rapidly into the outer layer of the cell membrane by the hydrolysosis of sphingomyelin by acidic or neutral sphingomyelinase (respectively ASM and NSM), but also in reticulum through a de novo synthesis pathway dependent of the ceramide synthase (5). Several studies demonstrate the involvement of ceramide in cell and tumor radiosensisitivity. Exogenous Ceramide treatment enhances radiation-induced LNCAP cell death and tumor regression (6). In the same manner, increasing endogenous ceramide through DL-PDMP and D-MAPP, respective inhibitors of glucosyl-ceramide synthase and ceramidase, enhances Jurkat radiosensitivity (7). Beside its involvement in tumor cell death, ceramide have been observed in endothelial cell apoptosis in response to high-dose radiation therapy which is modulating tumor regression. In fact, fibrosarcoma or melanoma tumor cells transplanted in mice, then irradiated, rapidly induced a massive endothelial cell apoptosis via ASM activation and ceramide generation participating to tumor regression (8). Invalidation of ASM blocks endothelial cell apoptosis and tumor regression induced by high dose radiation therapy.

Beside its intracellular form, secreted ceramide in the extracellular medium is also playing important biological roles in physiological and pathophysiological processes. High level of ceramide has been observed in plasma and serum from patients with several physiopathologies, including lung emphysema (9), Wilson disease (10), multiple organ failure (11). Plasma ceramide level is increased during lipid infusion in humans and rats, and in obese, insulin-resistant mice (12) which may correlated with insulin sensitivity, inflammation and atherosclerotic risk. Interestingly, ceramide and its enzyme ASM have also been quantified in serum from 11 patients with gross tumors from different origins after spatial fractionated grid radiation therapy (SF-GRT) including a first irradiation at 15 Gy followed by 30 fractions of 2 Gy (13). Three days after treatment increase of secreted ceramide was quantified in the serum of 5 of the 7 patients responding to this specific radiation therapy protocol. However, the few number of patients and the diverse origin of the tumors diluted the strength of their results and do not allow to establish strong statistical evidence the correlation of ceramide and radiation therapy efficacy.

SUMMARY OF THE INVENTION

The present invention relates to methods for determining whether a patient will achieve a response after radiation therapy. In particular, the present invention is defined by the claims.

DETAILED DESCRIPTION OF THE INVENTION

Discovering biological markers of tumor regression induced by ionizing radiation will permit a better discrimination between responding and refractory patients to the radiation therapy. In this present invention, the inventors studied the ability of plasmic ceramide, a known pro-apoptotic bioactive sphingolipid, to be correlated to the tumor control in a clinical phase II study combining hypofractionated radiation therapy and irinotecan in liver and lung metastases. Liver and lung metastases were indeed treated with 4 times 10 Gy at day 1, 3, 7 and 10 combined to 40 mg/m$^2$ of Irrinitocan at day 1 and 7. Plasma from patients was harvested before the first treatment and after the second and fourth treatments. After lipid extraction, ceramide was quantified by LC-MS/MS and correlated to radiation-induced tumor response. First, plasmic ceramide concentration was measured before irradiation and was not found to be related to the potential radiation therapy response. Then, the fold of ceramide concentrations was measured at day 3 or 10 versus the unirradiated baseline. Ceramide concentrations in patients responding to the radiation therapy were significantly up-regulated as compared to the non-responder patients. Finally, evaluation of the different subclasses of ceramide (in function of the number of carbons of the fatty acid chains), were estimated and demonstrated that the 4 major forms C16, C22, C24 and C24:1 ceramide were also upregulated in responders as compared to non-responders. In this present study, the inventors demonstrate that elevation of ceramide secreted in the plasma is correlated to the efficacy of the hypofractionated treatment.

Accordingly a first object of the present invention relates to a method for determining whether a patient suffering from a cancer will achieve a response after radiation therapy comprising the steps of i) determining the level of ceramide in a first blood sample obtained from the patient before radiation therapy, ii) determining the level of ceramide in a second blood sample obtained from the patient during or just after radiation therapy, iii) comparing the level determined at step i) with the level determined at step ii) and iv) concluding that the patient will achieve response when the level determined at step ii) is higher than the level determined at step i) or concluding that the patient will not achieve a response when the level determined at step ii) is lower than the level determined at step i).

Cancers to be treated include primary tumors and metastatic tumors. Examples of cancers that may be treated include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangio sarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The term "radiation therapy" has its general meaning in the art and refers the treatment of cancer with ionizing radiation. Ionizing radiation deposits energy that injures or destroys cells in the area being treated (the target tissue) by damaging their genetic material, making it impossible for these cells to continue to grow. One type of radiation therapy commonly used involves photons, e.g. X-rays. Depending on the amount of energy they possess, the rays can be used to destroy cancer cells on the surface of or deeper in the body. The higher the energy of the x-ray beam, the deeper the x-rays can go into the target tissue. Linear accelerators and betatrons produce x-rays of increasingly greater energy. The use of machines to focus radiation (such as x-rays) on a cancer site is called external beam radiation therapy. Gamma rays are another form of photons used in radiation therapy. Gamma rays are produced spontaneously as certain elements (such as radium, uranium, and cobalt 60) release radiation as they decompose, or decay. In some embodiments, the radiation therapy is external radiation therapy. Examples of external radiation therapy include, but are not limited to, conventional external beam radiation therapy; three-dimensional conformal radiation therapy (3D-CRT), which delivers shaped beams to closely fit the shape of a tumor from different directions; intensity modulated radiation therapy (IMRT), e.g., helical tomotherapy, which shapes the radiation beams to closely fit the shape of a tumor and also alters the radiation dose according to the shape of the tumor; conformal proton beam radiation therapy; image-guided radiation therapy (IGRT), which combines scanning and radiation technologies to provide real time images of a tumor to guide the radiation treatment; intraoperative radiation therapy (IORT), which delivers radiation directly to a tumor during surgery; stereotactic radiosurgery, which delivers a large, precise radiation dose to a small tumor area in a single session; hyperfractionated radiation therapy, e.g., continuous hyperfractionated accelerated radiation therapy (CHART), in which more than one treatment (fraction) of radiation therapy are given to a subject per day; and hypofractionated radiation therapy, in which larger doses of radiation therapy per fraction is given but fewer fractions.

In some embodiments, the method of the present invention is particularly suitable in the context of a hypo fractionated radiation therapy. As used herein the term "hypo fractionated radiation therapy" has its general meaning in the art and refers to radiation therapy in which the total dose of radiation is divided into large doses and treatments are given less than once a day.

Typically a treatment course comprises 1, 2, 3, 4 or 5 regimens of ionizing radiations. In some embodiments, the regimen of ionizing radiations is combined with the administration of at least one chemotherapeutic agent. Chemotherapeutic agent include those compounds with anti-cancer activity, e.g., compounds that induce apoptosis, compounds that reduce lifespan or compounds that render cells sensitive to stress and include but are not limited to aminoglutethimide, amsacrine, anastrozole, asparaginase, beg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, Ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

In some embodiments, the protocol of radiation therapy is performed on the patient as described in FIG. 1. Briefly, 4 sessions of 10 Gy (total dose: 40 Gy) were spread over 2 weeks at day 1, 3, 8 and 10 using a Novalis stereotaxic accelerator device. A dose of 40 mg/m$^2$ irinotecan (Pfizer) in 250 ml of physiological saline or glucose isotonic was intravenously injected 30 to 90 min before the first and third radiotherapy sessions. In this embodiment, the second blood sample is obtained at day 3.

By "blood sample" is meant a volume of whole blood or fraction thereof, eg, serum, plasma, etc.

As used herein the term "ceramide" has its general meaning in the art and refers to any N-acylsphingosine. Ceramides include sphingolipids in which the sphingosine is acylated with a fatty acid acyl CoA derivative to form an N-acylsphingosine. Typically, the carbon chain is saturated or unsaturated. Furthermore, the carbon chain comprises 16, 18, 20, 22 or 24 carbons. In some embodiments, the carbon chain is a C16, C16:1, C18, C18:1, C20, C20:1, C22, C22:1, C24, or C24:1 carbon chain.

Methods to determine the level of ceramide in biological samples are known in the art, for example, as provided in Kasumov et al, "Quantification of Ceramide Species in Biological Samples by Liquid Chromatography-Electrospray Tandem Mass Spectrometry," Anal. Biochem. 401(1): 154-161 (2010) or Hu, W., et al, (2009) J. Lipid. Res. 50, 1852-1862, herein incorporated by reference in their entireties. Typically, quantitative analyses of ceramides is performed by Ultra Performance Liquid Chromatography coupled to a mass spectrometer. Immunoassays are also possible and generally involve contacting the blood sample with an antibody to ceramide, under conditions effective to allow the formation of immunocomplexes. In this regard, the skilled artisan will be able to assess the level of ceramide in the blood sample.

In some embodiments, the level of total ceramide is determined. In some embodiments, the level of at least one ceramide subspecies is determined. In some embodiments, the subspecies is selected from the group consisting of C16, C16:1, C18, C18:1, C20, C20:1, C22, C22:1, C24, or C24:1 ceramides. In some embodiments, the level of C24 ceramide is determined.

The method of the present invention is particularly suitable for discriminating responder from non responder. As used herein the term "responder" in the context of the present disclosure refers to a patient that will achieve a response, i.e. a patient where the cancer is eradicated, reduced or improved. According to the invention, the responders have an objective response and therefore the term does not encompass patients having a stabilized cancer such that the disease is not progressing after radiation therapy. A non-responder or refractory patient includes patients for whom the cancer does not show reduction or improvement after radiation therapy. According to the invention the term "non responder" also includes patients having a stabilized cancer. Typically, the characterization of the patient as a responder or non-responder can be performed by reference to a standard or a training set. The standard may be the profile of a patient who is known to be a responder or non responder or alternatively may be a numerical value. Such predetermined standards may be provided in any suitable form, such as a printed list or diagram, computer software program, or other media. When it is concluded that the patient is a non responder, the physician could take the decision to stop the protocol or radiation therapy to avoid any further adverse sides effects.

The invention will be further illustrated by the following figures and examples. However, these examples and figures should not be interpreted in any way as limiting the scope of the present invention.

FIGURES

FIG. 1. Treatment plan of the phase II clinical protocol combining SBRT with irinotecan. Irradiations (10 Gy) were applied at D1, D3, D7 and D10. Irinotecan (40 mg/m$^2$) was administered at D1 and D7. Blood samples were harvested before treatment (D0) and after the second and fourth irradiation (D3 and D10).

FIG. 2. Variation of total Cer during the treatment is correlated with the tumor response. A. Ratio of Cer concentration at D3 and D10 vs. D0 in complete responder (CR), partial responder (PR), tumor stabilization (S) and progression (P) groups. B. Ratio of the Cer concentration at D3 and D10 vs. D0 in tumor responding (CR, PR, and S) group as compared to tumor progression (P) group. C. Ratio of the Cer concentration at D3 and D10 vs. D0 in tumor shrinking (CR, PR) group as compared to the group where tumors do not regressed (S, P). Measurements were performed in triplicate (Number of patients in parentheses, mean±SEM, ns=$P>0.05$, *=$P<0.05$).

FIG. 3. Evolution of major Cer subspecies during the treatment is correlated with the tumor response. Ratio of C16:0 (A), C22:0 (B), C24:0 (C), and C24:1 Cer (D) concentrations at D3 and D10 vs. D0 in objective response (CR, PR) group as compared to the refractory group (S, P). Measurements were performed in triplicate (Number of patients in parentheses, mean±SEM, ns=P>0.05, *=P<0.05).

Figure 4:
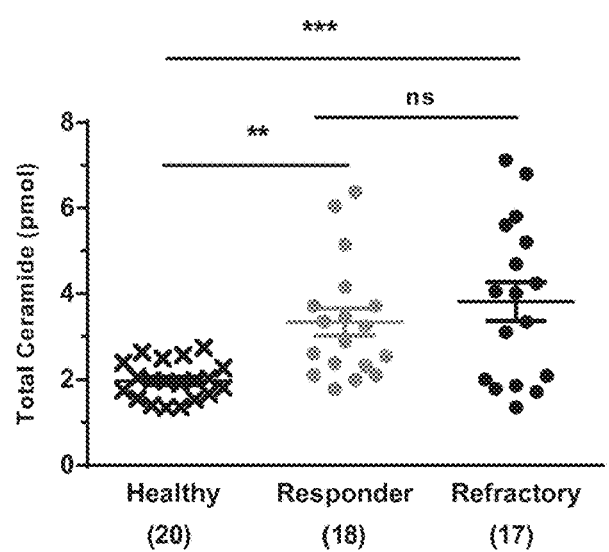

FIG. 4. Basal Cer level does not correlated with the outcome of the radiotherapy. Basal plasma Cer was measured in responder and refractory patients and healthy population were performed in triplicate (mean±SEM, ns=P>0.05, *=P<0.05).

Figure 5:
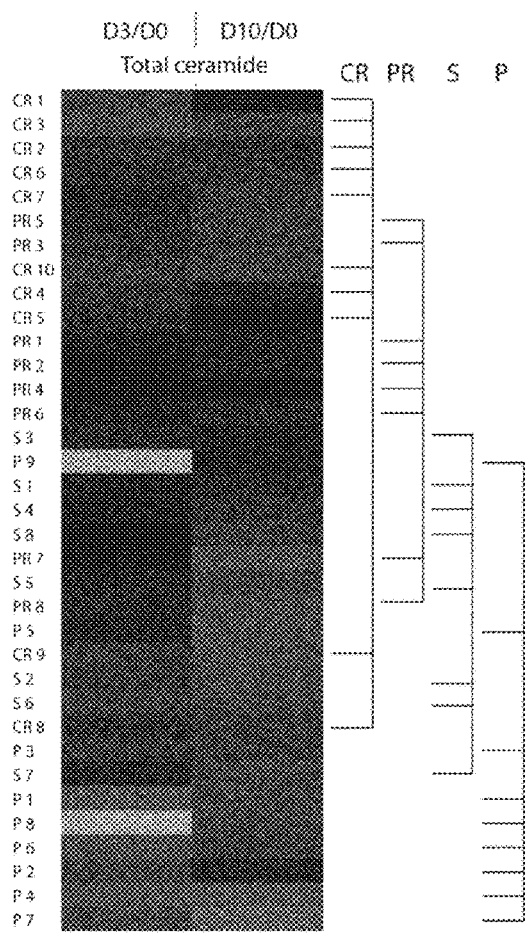

FIG. 5. Hierarchization of Cer variation clusters patients in function of their tumor response. CER increases and decreases at D3 and D10 respectively are represented in red and green where median equal to 0 are in black. The position of each patient on the hierarchy is presented after cluster 3.0 analysis and tree view visualization as function of tumor response to the treatment (CR, PR, S, P).

Figure 6A:
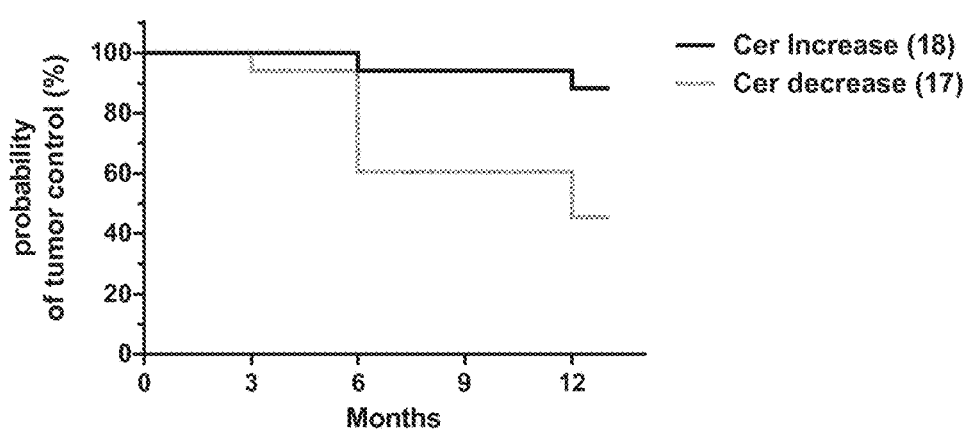
Figure 6B:
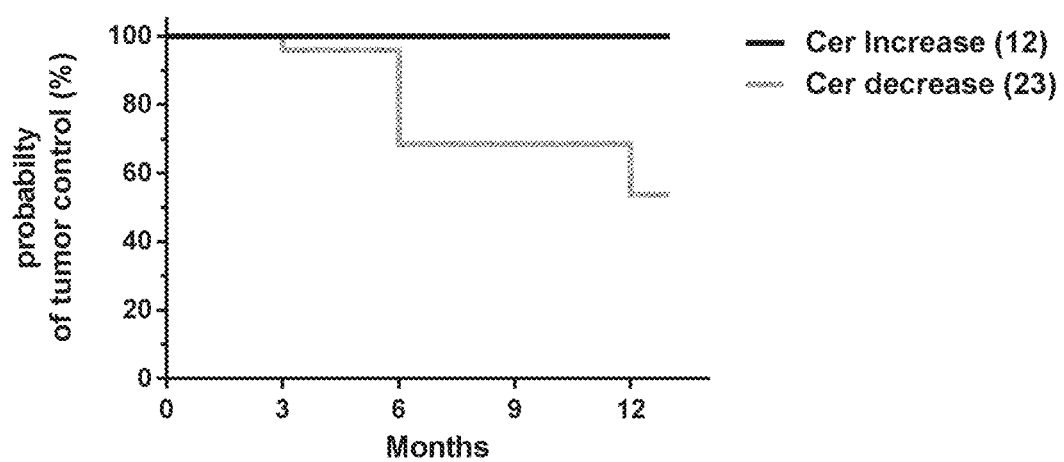

FIG. 6. Cer modulation during the treatment discriminate tumor control in function of time. Kaplan-Meier curves for patients without tumor volume worsening in function of time are shown for patients with either an increase or decrease of Cer at D3 (A) and D10 (B). Number of patients are in parentheses. P<0.05 between groups Cer increase and Cer decrease for both figures.

EXAMPLE

Material & Methods

Patient Selection Criteria and Follow-up

A multicentric phase II clinical study with SBRT and concomitant irinotecan for colorectal adenocarcinoma lung and liver metastases relapsing from Fluorouracil (5-FU) with or without eloxatin or irinotecan, was performed from 2008 to 2013 between 3 French oncology centers (Nantes, Lyon, and Lille). Patients (mean age, 64 years; range, 32-80 years), with a life expectancy over 6 months and with an inoperable or recurrent hepatic and/or lung metastases after surgery were selected. Metastases should be measurable with the largest diameter under or equal to 6 cm. The sum of the maximum diameter of multiple metastases must be under or equal to 6 cm. Clinical target volume (CTV) should be located more than 12 mm laterally or 15 mm in the cranio-caudal direction of stomach, small intestine esophagus, trachea, and pulmonary arteries.

Patients must have an adequate hematologic cell pool (over $1.5 \times 10^9$ white cells, $10^{11}$ platelets and 90G hemoglobin $L^{-1}$), and adequate hepatic and renal functions (serum bilirubin less than 1.5 fold and transaminase and alkaline phosphatase less than 5-fold over the upper limit of normal). Exclusion criteria were defined as a performance index according to the World Health Organization (WHO) scale greater than 2, prior thoraco-abdominal irradiation, a contraindication to irinotecan prior (within 5 years) or concomitant treatment of an invasive cancer, diffuse metastatic disease, or more than 3 metastases. All institutional ethics committees approved the protocol, and signed informed consents were obtained from all patients.

Treatment and Plasma Collection

The complete treatment protocol is described in FIG. 1. Briefly, 4 fractions of 10 Gy were spread at day (D)1, 3, 8 and 10 using Novalis (Brain Lab, Feldkirchen, D) or Cyberknife (Accuray, Sunnyvaley, Calif.) stereotactic accelerator devices. Whatever the type of accelerator, 99% CTV was encompassed by 75-95% isodose corresponding to a dose from 42 to 53 Gy at the center. Forty mg/m$^2$ irinotecan (Pfizer, New York, N.Y.) was intravenously injected 30 to 90 min before the first and third radiotherapy sessions. Because of the absence of toxicity, the 35 patients received the complete treatment. Twenty ml of blood was collected in tubes with citrate before the first (D0) and after second (D3) and fourth (D10) irradiations, then stored at 4° C. for 30 min. Blood samples were centrifuged at 1000 g for 5 min at 4° C. to recover the plasma. Plasma aliquots were stored at −80° C. until further analysis. Whole blood from healthy donors over 45 years, were collected at the French blood institute (EFS, Nantes, F), to recover the plasma using the same protocol as previously described.

Response Criteria

The tumor response to the protocol was assessed using RECIST 1.1 (Response Evaluation Criteria In Solid Tumors) on the thoracic or liver tomodensitometry (TDM) (Eisenhauer et al, 2009). The first evaluation was performed 6-8 weeks after the end of treatment, then at 3, 6, and 12 months. A complete response (CR) was defined by the complete disappearance of all lesions. A partial response (PR) and a progression (P) were respectively characterized by a reduction greater than 30% and an increase greater than 20% of the largest diameters of each lesion. Stability (S) was declared when tumor reduction or progression was respectively insufficient to define a PR or a P.

Cer Analysis

Materiel

Ultrapure standards of Cer subspecies (C14:0, C16:0, C18:0, C18:1, C20:0, C24:0 and C24:1) and non-natural C17:0 Cer used as an internal standard (IS) were purchased from Avanti Polar Lipids (Alabaster, Ala.). UPLC grade methanol and analytical grade organic solvents were purchased from Fisher Scientific (Pittsburgh, Pa.).

Extraction

Forty microliters from 1 µM C17 Cer were added to each sample. Lipid extraction was carried out in two steps with minor modifications of previously described procedures (Hara & Radin, 1978). First extraction was performed by adding 1.5 ml of hexane/propan-2-ol mixture (60:40, V/V) on 100 µl of plasma. The sample was vortexed, centrifuged at 3000 g for 5 min at 4° C. and the upper phase was collected. A second extraction was then performed with 1.5 ml of methanol. After homogenization and centrifugation at 8000 g for 5 min at 4° C., the upper phase was collected, combined with the first, dried under nitrogen at room temperature and resuspended in 150 µl of hexane/propan-2-ol (60:40 v/v).

Purification

Lipid extract purification was optimized from a previous method (Bodennec et al, 2000). Briefly, samples were loaded on LC-NH$_2$ cartridges (Interchim, Montluçon, F) preconditioned with 2 ml of hexane. The 100 mg cartridge was washed with 1.4 ml of ethyl acetate-hexane 15:85 (v/v) eluting neutral lipids in a single fraction. A second wash with 1.6 ml of chloroform/methanol 23:1 (v/v) eluted free Cer. Cer fraction was dried down under nitrogen and redissolved in 300 µl of MeOH containing 10 mM highest grade ammonium acetate (Fluka, Buchs, CH) and 0.2% formic acid. Samples were stored at −20° C. until analysis.

Mass Spectrometry Analysis

Purified Cer fractions were analyzed by LC-ESI-MS/MS on an Acquity H-Class UPLC system combined with a Xevo TQD triple quadrupole mass spectrometer (Waters Corporation, Milford, Conn.). Gradient chromatographic separation was performed on Waters C18 BEH column (2.1 mm×50 mm) with 1.8 µM particle size equipped with a 0.5 µM prefilter. The column heater was set at 43° C. The mobile phases consisted of MiliQ water containing 0.2% formic acid and 10 mM ammonium acetate (Eluent A) and methanol containing 0.2% formic acid and 10 mM ammonium acetate (Eluent B). The injection volume was 5 µl. Purified Cer were eluted in 4 min with a linear gradient to 98% of eluent B. Before the next run, a reequilibration from 4.00 to 4.10 min and stabilization from 4.10 to 6 min with 95% of eluent B were performed. The flow rate was set to 0.6 ml/min. All analyses were performed using electrospray ionization in the positive ion mode with multiple reactions monitoring (MRM). Measurement and data analysis were collected by Mass-Lynx software version 4.1. Integration and quantification were performed using the Waters Target Links™ software.

Statistical Analysis and Data Clustering

Three independent measurements were performed per patient sample. Wilcoxon signed-rank test and ANOVA with 95% confidence estimation were performed with StatView 6.0 package. For Hierarchical clustering, Cer ratios between D3 or D10 and D0 were estimated according to the expression profiling of other patients (Eisen et al, 1998) by cluster 3.0 and displayed by Java TreeView (both softwares, http://bonsai.hgc.jp/~mdehoon/software/cluster/software.htm). Independence of each group was tested by chi squared test. The probability of tumor control in function of time in patient with an increase or decrease of ceramide were obtained by Kaplan-Meier method (Kaplan, 1958) and compared by the log-rank test, giving 95% confidence intervals (CI). The prognostic value of variables (sex, age, tumor location and volume) was calculated using the Cox multivariate regression model (Cox, 1972).

Results

Figure 2A:
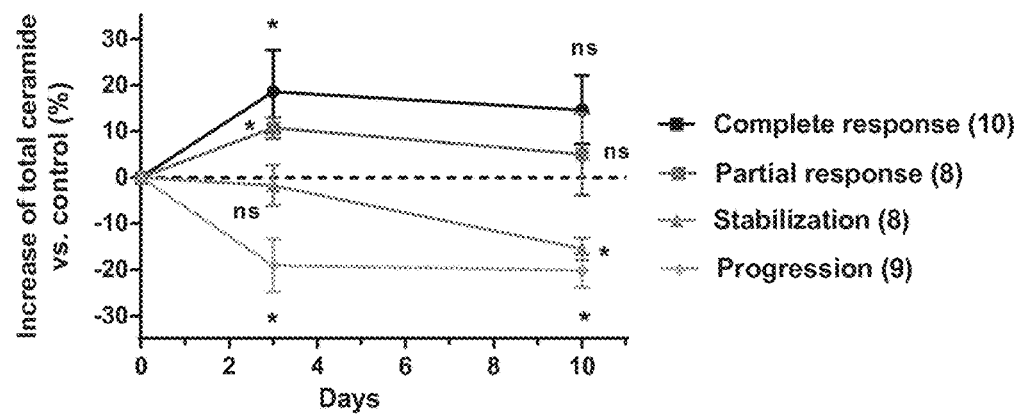

Variation of Total Cer During the Treatment is Correlated with the Tumor Response Concentration of plasma Cer was monitored by LC-ESI-MS/MS during the SBRT protocol with irinotecan, at D3 and D10 and then, compared to the basal level at D0 (FIG. 2). First, no correlation was shown between the level of Cer increase at D3 and D10 after SBRT with irinotecan and any covariance factors (sex, age, tumor location and tumor volume; data not shown). Then, mean increase of Cer concentration in the different patient groups was monitored in function of their tumor response (FIG. 2A). One year after treatment, CR was observed in 10, PR in 8, S in 8 and P in 9 patients. We observed that Cer dose response at D3 and D10 correlated with treatment efficacy. The total Cer amount increased significantly at D3 in plasma from patients exhibiting a diminution of tumor volume (CR: 18.5%±8.92, $P<0.05$ and PR: 10.7%±2.27; $P<0.01$; both vs. D0). In contrast, total Cer in S group remained stable at D3, then decreased significantly at D10 (D3: −1.70%±4.36; $P>0.05$ and D10: −15%±2.40; both $P<0.01$ vs. D0) and was below the basal level for the P group (D3: —19.06%±5.72; $P<0.05$ and D10: −20.16%±3.71; both $P<0.01$ vs. D0).

Figure 2B:
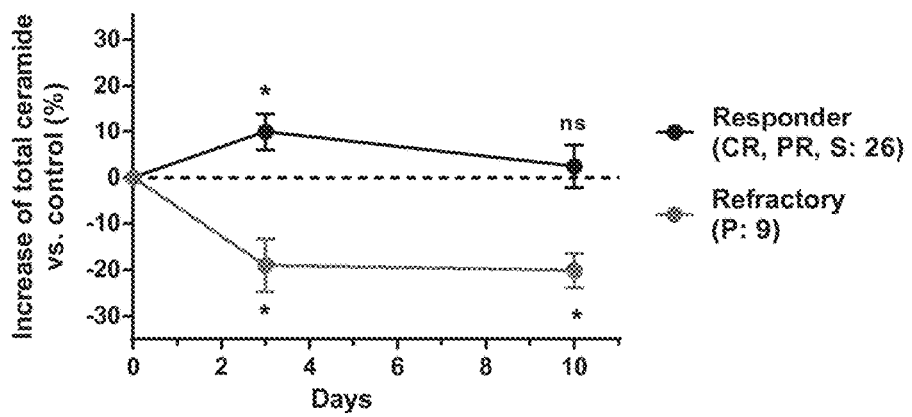
Figure 2C:
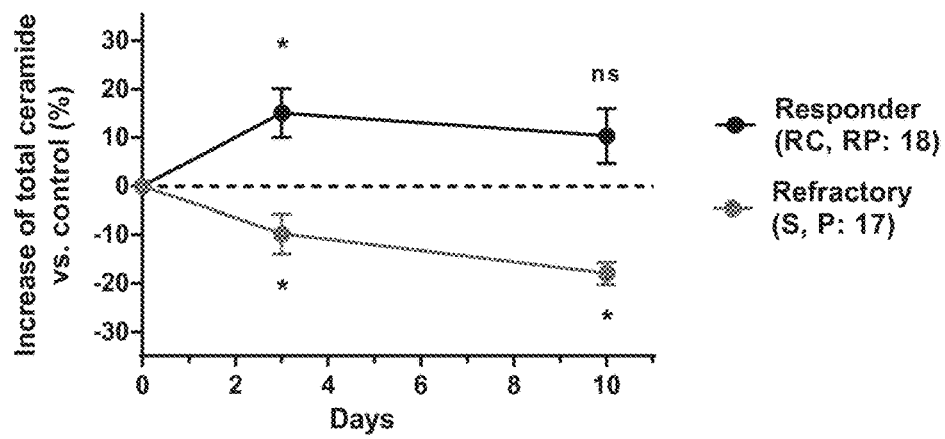
Figure 3A:
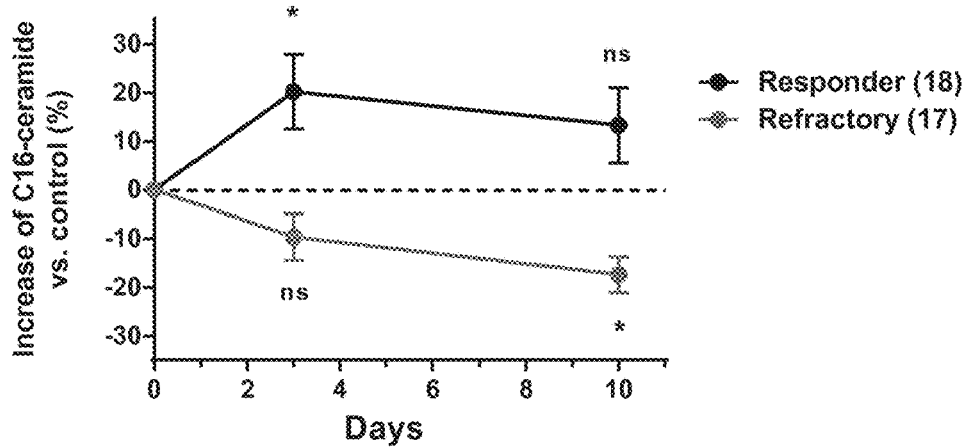
Figure 3B:
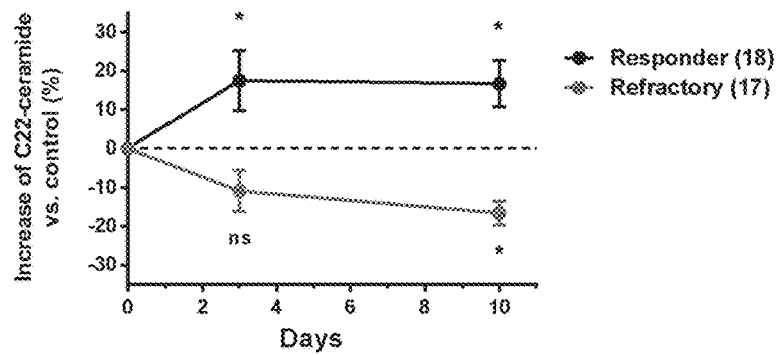
Figure 3C:
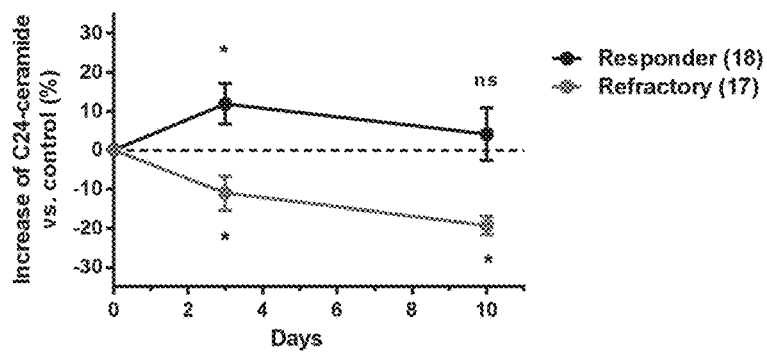
Figure 3D:
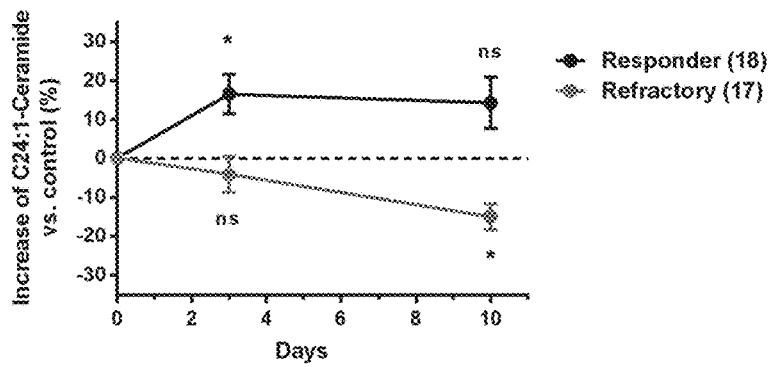

Because the tumor growth arrest is a hallmark of the response to the treatment, we first decided to determine a potential correlation between responders including CR, PR and S groups, and refractory patients including P group (FIG. 2B). The total Cer level of this responding group (CR, PR, and S) was significantly higher in comparison to the basal level at D3 (9.91%±3.99; $P<0.05$ vs. D0), but not to D10. Interestingly, the total Cer level of this refractory group (P) decreased significantly at D3 and D10 compared to the basal rate (D3: −19.06%±5.72; $P<0.05$ vs. D0; and D10: −20.17%±3.71; $P<0.01$ vs. D0). As proposed in the present clinical phase II study, CR and PR were defined as the objective response where S and P were considered as refractory to the treatment (FIG. 2C). One year after treatment, 18/35 patients exhibited an objective response whereas 17/35 patients were considered refractory, due to tumor stabilization or progression or the emergence of new pulmonary or liver metastases. Using this classification group, the total Cer level of the objective responder group was significantly higher in comparison to the basal Cer level objective group at D3 (15.07%±5.02; $P<0.01$ vs. D0), and significantly lower for refractory group at D3 and D10 (D3: −9.79%±4.12; $P<0.05$ vs. D0 and D10: −17.95%±2.27; $P<0.01$ vs. D0). The increase of plasma Cer concentration during the SBRT combined with irinotecan represents a promising endpoint that many serve as a harbinger tumor regression. On the other hand, the decrease of plasma Cer concentration is associated with the lack of tumor response of the treatment.

Evolution of Major Cer Subspecies During the Treatment is Correlated with the Tumor Response Twelve Cer subspecies, have been sought in order to characterize more specifically the composition of the total Cer. The most abundant compounds were those containing the fatty acid C24:0 (45.46%±1.06), C24:1 (23.43%±0.90), C22:0 (15.74%±0.34), and C16:0 (7.10%±0.39). The other compounds were present in very small amount (FIG. S1). Because of a potential discrepancy of their response to the treatment, those major Cer subspecies were separately quantified, compared to their basal level at D0 and correlated with the tumor response (FIG. 3A to D). In fact, the levels of these 4 subspecies followed a similar profile as that of the total Cer levels during the treatment. The ratio of C24:0 Cer, the most abundant compound, increased significantly in the objective responder group from 11.9%±5.17 at D3 ($P<0.05$ vs. D0). These subspecies decreased significantly in the refractory group from −11.08%±4.33 at D3 and -19.19%±2.39 at D10 (both $P<0.05$ vs. D0). The three other main Cer subspecies exhibited similar significant changes in their ratios as observed for C24:0 Cer. These results establish that all the major plasma Cer subspecies, as well as the total Cer, are evolving following a similar pattern of change after SBRT combined with irinotecan, with rising levels correlated with the tumor response.

Basal Cer Level does not Correlated with the Outcome of the Radiotherapy

Because plasma Cer appears to hold promise as a surrogate marker of the tumor response, correlation of basal level of Cer in patients with treatment efficacy was investigated. Plasma Cer concentration from healthy donors was very homogenous and significantly lower (mean: 1.98 µM±0.09) than that of the patients with high individual variability (responder group: 3.34 µM±0.32 and refractory group 3.82 µM±0.45; both $P<0.01$ vs. healthy donors). Basal Cer concentration appears as a marker of tumor presence in patients. However, the comparison of the total CER concentration between the 2 patient groups did not permit a discrimination between the responder group and the refractory group ($P=0.67$). Thus, the amount of total Cer in patients before any treatment cannot be regarded as a prognostic factor of the tumor response to SBRT combined to irinotecan.

Hierarchization of Cer Variation Clusters Patients in Function of their Tumor Response Total Cer and its subspecies modulation during treatment were evaluated for each patient and hierarchical clustering was established. Cer increased and decreased at D3 and D10 are represented respectively in red and green when median equal to 0 are in black (FIG. 5). Clustering of the individual Cer evolution demonstrated a hierarchy between patients with objective and refractory responses. Hierarchy of total Cer modulation at D3 and D10 showed clearly that 8/10 CR and 6/8 PR patients are clustered above the median response equal to 0 (both P<0.001). In contrast, 5/8 S and 8/9 P patients were grouped below this median (both P<0.001). For every Cer subspecies, a similar discrimination between the objective and refractory patients were obtained (data not shown) without improvement of the patients' segregation as compared to the cluster analysis with total Cer.

Cer Modulation During the Treatment Discriminate Tumor Control in Function of Time Finally, we evaluated the tumor volume worsening measured by CT-Scan 3, 6 and 12 months after treatment in function of the evolution of total Cer in blood plasma (FIG. 6). Kaplan Meier curves clearly demonstrate that patients with increase of Cer either at D3 or D10 get high probability of tumor control during the first year. Interestingly, no patients with Cer increase at D10 show an aggravation of tumor. Patients with decrease of Cer have a 50% of chance to tumor worsening during the first year. These results clearly and statistically discriminates the ability of tumor control for treated patients in function of early Cer increase or decrease (D3 or D10: p<0.01).

Discussion

In the present well-defined phase II study combining SBRT with irinotecan, we clearly correlated the elevation of Cer concentration in the blood plasma with the tumor response rate. Similarly, a decrease of Cer concentration in the blood plasma was correlated with stabilization or a tumor progression, and therefore within effective treatment. Our results defined plasma Cer as an early surrogate marker of the tumor response, detectable early during the radiotherapy treatment.

The results presented in FIG. 3, show that patients with liver or lung metastases of colorectal cancer, have a Cer concentration in blood plasma higher than healthy patients. These results are in agreement with the literature showing a modulation of Cer in the patient's blood suffering from diverse pathologies (Delogu et al, 1999; Lang et al, 2007; Petrache et al, 2005; Watt et al, 2012). Moreover, Cer in the blood flow has also been quantified after SFGRT scheme including a fraction of 15 Gy then 30 of 2 Gy (Sathishkumar et al, 2005). Plasma Cer concentrations were significantly increased 72 h after SFGRT in 3/3 CR and 2/4 PR patients. However, no correlation was found in the no-responder group where one patient showed an increase of Cer level, and the other one a decrease. Indeed, significant discrimination Cer increase and decrease groups was impossible because of the small size of the cohort. Furthermore, the diverse tumor origins diluted the strength of the results. This promising study was not allowing statistical evidence establishing the secreted Cer as a biomarker of radiotherapy efficacy.

In the present study, those two weaknesses have been solved. First, our study includes a larger cohort of 35 patients with almost an equal number of responders and refractory (respectively 18 and 17). Secondly, all metastases derived from primary colorectal carcinoma and were treated by SBRT with irinotecan. Finally, the tumor volumes were equivalent, below 6 cm for the largest diameter limiting potential inconsistency due to the volume size. Because of the strict patient inclusion criteria and clinical follow-up, we were able to extend previous results on the correlation between modulation of the total Cer into the blood stream and the tumor response after radiotherapy. Moreover, our work sheds new light on the Cer subspecies enhanced after irradiation. In fact, not only total Cer, but all the abundant Cer subspecies (C16:0, C18:0, C22:0, C22:1, C24:0, and C24:1, Cer) were increased in the responder group (FIGS. 4 and S2). Surprisingly, the decreases of all Cer subspecies in the plasma from the refractory group were observed mainly at D10 and not D3. Interestingly, total Cer evolution is sufficient to evaluate the efficacy response after SBRT with irinotecan. The quantification and the analysis of the different Cer subspecies do not improve the strength of the biomarker properties. This finding was confirmed by clustering analysis. In fact, 8/10 CR and 6/8 PR patients were above the median of the total Cer modulation at D3 and D10, when 7/8 S and 8/9 P patients were below (FIG. 5). Chi square statistic test demonstrated that the increase of plasma Cer is higher in objective responder than refractory patients (P<0.01). No advantage was gained by measuring the different subspecies individually. So, total Cer represents a reliable early biomarker for individual response to radiotherapy.

The high concentration of Cer into the blood stream may be explained by different mechanisms. ASM and Cer are secreted into the extracellular medium, by endothelial cells activated by pro-inflammatory cytokines including Il-$\beta$ or TNF-$\alpha$ (Marathe et al, 1998). We also found that irradiation of primary micro-vascular endothelial cells HMVEC-L induces secretion of ASM and Cer into the extracellular medium (data not shown). In this hypothesis, Cer release by endothelial activation may lead to subsequent Cer-dependent radiosensitization of the tumor cells. The elevation of plasma Cer may also due to the high level of tumor apoptotic bodies enriched in Cer induced by the SBRT with irinotecan. Non-regulated of increase Cer may appear during late non-reversible stage of DNA damage-induced cell death (Tepper et al, 1999). The high level of Cer in the blood stream could be a marker of this form of cell death. In fact, we showed a correlation between the strength of tumor regression resulting from cell death and the increase of plasma Cer after SBRT and irinotecan (FIG. 2A). We are presently looking for a correct biological explanation for elevation of plasma Cer. Further studies must also define the specific role of SBRT and irinotecan treatment in the secretion of Cer.

Because of our findings, we proposed that plasma Cer concentration represents an early biomarker of response efficacy SBRT and irinotecan. This statement is supported by the fact that neither sex, age, location nor tumor volume was a co-variance factor correlated with the increase of ceramide during treatment. Preliminary data shows that tumor irradiation in mice induces plasma Cer in a dose-dependent manner (data not shown). We must reproduce the experiments using irinotecan to estimate its ability to induce plasma Cer.

So, finding early surrogate markers may allow physicians to adapt or stop the treatment, limiting potential complications associated with treatments that do not have clinical benefits. Furthermore, early biomarkers allowing adaptation of the tumor treatment will permit a personalized therapy by reducing the cost of the treatment and the arrest of expensive targeted therapy, if necessary. Further investigations will be required to demonstrate if our finding can be generalized to other radiotherapy protocols. Common radiotherapy protocols are designed using a fractionated dosing schedule of 2 Gy daily for several weeks. It is still not clear whether conventional fractionation is inducing intracellular Cer inside the irradiated cells. The 2 Gy per day dose of radiation may not be enough to generate Cer. Furthermore, as already seen on the tumor cell death, the Cer generation might be occurring slowly over the course of several weeks of the treatment and thus changes over baseline may not reach the level of significance. Further clinical studies must validate or refute Cer as a tumor response surrogate marker after conventional radiotherapies. The new radiotherapy devices (stereotaxic X-ray accelerator, intrabeam, protontherapy) allow better tumor targeting. As a consequence, clinical protocols are being re-evaluated and redesigned for some tumor exposures, with a dose escalation and a decrease in the number of fractions. By increasing the dose, intracellular Cer generation and/or tumor cell death is enhanced. In this case, plasma Cer levels would be expected acutely after irradiation improving its detection. Because of those specificities, increase of plasma Cer might only be observable and quantifiable after high dose radiation.

Finally, this study providing an important and timely insight of the plasma ceramide impact in tumor response to SBRT with irinotecan might be translated into an improvement in the clinical management of similar patients. Our Kaplan Meier analyses shows a statistical discrimination of tumor control in patients, defined by CT-Scan over the first year of treatment, and the plasma Cer elevation or diminution (FIG. 6). Moreover, plasma Cer concentration at D10 seems more truthful to estimate the probability of patient to prolong tumor control over the year. When Cer decrease at D3 or D10, tumor volume in 50% of patients will increase proving a failure of the therapy during or just at the end of the treatment. Tumor volume assessment by MRI, CT-Scan or PET-SCAN may be observed but only months after treatment. This limits the usage of new treatments for refractory patients and increases the risk of tumor progression and complications of ineffective treatments. Early diagnostic biomarkers of the tumor response during the radiotherapy may influence physicians to adapt or to stop inefficient treatments. Moreover, patients will be reassured rapidly of their treatment efficacy. In this circumstance, the modulation of secreted Cer in blood flow represents a new and interesting early biomarker of tumor response to clinical radiotherapy protocols using high dose per fraction.

REFERENCES

Throughout this application, various references describe the state of the art to which this invention pertains. The disclosures of these references are hereby incorporated by reference into the present disclosure.

Bernier J, Hall E J, Giaccia A (2004) Radiation oncology: a century of achievements. *Nat Rev Cancer* 4(9): 737-47

Bibault J E, Ceugnart L, Prevost B, Mirabel X, Lartigau E (2013) CT appearance of pulmonary carcinomas after stereotactic radiation therapy. *Diagnostic and interventional imaging* 94(3): 255-62

Bodennec J, Koul O, Aguado I, Brichon G, Zwingelstein G, Portoukalian J (2000) A procedure for fractionation of sphingolipid classes by solid-phase extraction on aminopropyl cartridges. *J Lipid Res* 41(9): 1524-31

Corre I, Niaudet C, Paris F (2010) Plasma membrane signaling induced by ionizing radiation. *Mutat Res* 704(1-3): 61-7

Cox D R (1972) Regression models and life tables. *J R Stat Soc* 34: 187-220

Delogu G, Famularo G, Amati F, Signore L, Antonucci A, Trinchieri V, Di Marzio L, Cifone M G (1999) Ceramide concentrations in septic patients: a possible marker of multiple organ dysfunction syndrome. *Crit Care Med* 27(11): 2413-7

Eisen M B, Spellman P T, Brown P O, Botstein D (1998) Cluster analysis and display of genome-wide expression patterns. *Proc Natl Acad Sci USA* 95(25): 14863-8

Eisenhauer E A, Therasse P, Bogaerts J, Schwartz L H, Sargent D, Ford R, Dancey J, Arbuck S, Gwyther S, Mooney M, Rubinstein L, Shankar L, Dodd L, Kaplan R, Lacombe D, Verweij J (2009) New response evaluation criteria in solid tumours: revised RECIST guideline (version 1.1). *Eur J Cancer* 45(2): 228-47

Ganepola G A, Nizin J, Rutledge J R, Chang D H (2014) Use of blood-based biomarkers for early diagnosis and surveillance of colorectal cancer. *World J Gastrointest Oncol* 6(4): 83-97

Garcia-Barros M, Paris F, Cordon-Cardo C, Lyden D, Rafii S, Haimovitz-Friedman A, Fuks Z, Kolesnick R (2003) Tumor response to radiotherapy regulated by endothelial cell apoptosis. *Science* 300(5622): 1155-9

Hara A, Radin N S (1978) Lipid extraction of tissues with a low-toxicity solvent. *Anal Biochem* 90(1): 420-6

Kaplan E S M, P. (1958) Non parametric estimation from incomplete observation. *J Am Stat Assoc* 53: 457-480

Kavanagh B D, Miften M, Rabinovitch R A (2011) Advances in treatment techniques: stereotactic body radiation therapy and the spread of hypofractionation. *Cancer J* 17(3): 177-81

Kimura K, Markowski M, Edsall L C, Spiegel S, Gelmann E P (2003) Role of ceramide in mediating apoptosis of irradiated LNCaP prostate cancer cells. *Cell Death Differ* 10(2): 240-8

Kumar S, Mohan A, Guleria R (2006) Biomarkers in cancer screening, research and detection: present and future: a review. *Biomarkers* 11(5): 385-405

Lang P A, Schenck M, Nicolay J P, Becker J U, Kempe D S, Lupescu A, Koka S, Eisele K, Klarl B A, Rubben H, Schmid K W, Mann K, Hildenbrand S, Hefter H, Huber S M, Wieder T, Erhardt A, Haussinger D, Gulbins E, Lang F (2007) Liver cell death and anemia in Wilson disease involve acid sphingomyelinase and ceramide. *Nat Med* 13(2): 164-70

Malviya G, Nayak T K (2013) PET imaging to monitor cancer therapy. *Curr Pharm Biotechnol* 14(7): 669-82

Marathe S, Schissel S L, Yellin M J, Beatini N, Mintzer R, Williams K J, Tabas I (1998) Human vascular endothelial cells are a rich and regulatable source of secretory sphingomyelinase. Implications for early atherogenesis and ceramide-mediated cell signaling. *J Biol Chem* 273(7): 4081-8

Petrache I, Natarajan V, Zhen L, Medler T R, Richter A T, Cho C, Hubbard W C, Berdyshev E V, Tuder R M (2005) Ceramide upregulation causes pulmonary cell apoptosis and emphysema-like disease in mice. *Nat Med* 11(5): 491-8

Rodriguez-Lafrasse C, Alphonse G, Aloy M T, Ardail D, Gerard J P, Louisot P, Rousson R (2002) Increasing endogenous ceramide using inhibitors of sphingolipid metabolism maximizes ionizing radiation-induced mitochondrial injury and apoptotic cell killing. *Int J Cancer* 101(6): 589-98

Sathishkumar S, Boyanovsky B, Karakashian A A, Rozenova K, Giltiay N V, Kudrimoti M, Mohiuddin M, Ahmed M M, Nikolova-Karakashian M (2005) Elevated sphingomyelinase activity and ceramide concentration in serum of patients undergoing high dose spatially fractionated radiation treatment: implications for endothelial apoptosis. *Cancer Biol Ther* 4(9): 979-86

Tepper A D, de Vries E, van Blitterswijk W J, Borst J (1999) Ordering of ceramide formation, caspase activation, and mitochondrial changes during CD95- and DNA damage-induced apoptosis. *J Clin Invest* 103(7): 971-8

Watt M J, Barnett A C, Bruce C R, Schenk S, Horowitz J F, Hoy A J (2012) Regulation of plasma ceramide levels with fatty acid oversupply: evidence that the liver detects and secretes de novo synthesised ceramide. *Diabetologia* 55(10): 2741-6

The invention claimed is:

1. A method for treating a patient suffering from a cancer and identified as a radiotherapy responder comprising the steps of
   i) determining the level of ceramide in a first blood plasma or blood serum sample obtained from the patient before a first regimen of ionizing radiation,
   ii) treating the patient suffering from a cancer with a first and a second regimen of ionizing radiations,
   iii) determining the level of ceramide in a second blood plasma or blood serum sample obtained from the patient after the second regimen of ionizing radiation,
   iv) comparing the level determined at step i) with the level determined at step iii), thereby identifying the patient as a radiotherapy responder when the level of ceramide determined at step iii) is at least 10% higher than the level of ceramide determined at step i), and
   v) treating the patient suffering from a cancer and identified at step iv) as a radiotherapy responder with further regimens of ionizing radiation.

2. The method of claim 1 wherein the cancer to be treated is selected from the group consisting of primary tumors and metastatic tumors.

3. The method of claim 1 wherein the cancer is selected from the group consisting of cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, and uterus.

4. The method of claim 1 wherein the cancer is selected from the group consisting of neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

5. The method of claim 1 wherein the radiation therapy consists of a hypofractionated radiation therapy.

6. The method of claim 1 wherein the treatment course comprises 2, 3, 4 or 5 regimens of ionizing radiations.

7. The method of claim 1 wherein the regimen of ionizing radiations is combined with the administration of at least one chemotherapeutic agent.

8. The method of claim 7 wherein the chemotherapeutic agent is selected from the group consisting of aminoglutethimide, amsacrine, anastrozole, asparaginase, beg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

9. The method of claim 1 wherein the protocol of radiation therapy consists of 4 regimens of 10 Gy spread over 2 weeks at day 1, 3, 8 and 10 using combined with the administration of a dose of irinotecan injected 30 to 90 minutes before the first and third regimen of ionizing radiation.

10. The method of claim 9 wherein the second blood plasma or blood serum sample is obtained at day 3.

11. The method of claim 1 wherein the level of ceramide is determined by Ultra Performance Liquid Chromatography coupled to a mass spectrometer.

12. The method of claim 1 wherein the level of total ceramide is determined.

13. The method of claim 1 wherein the level of at least one ceramide subspecies is determined wherein the subspecies is selected from the group consisting of C16, C16:1, C18, C18:1, C20, C20:1, C22, C22:1, C24, and C24:1 ceramides.

14. The method of claim 1 wherein the level of C24 ceramides is determined.

15. The method of claim 1 wherein the level of C16, C22, C24 and C24:1 ceramide is determined.

* * * * *